US00PP24925P3

(12) United States Plant Patent
Madsen

(10) Patent No.: US PP24,925 P3
(45) Date of Patent: Sep. 23, 2014

(54) ***CAMPANULA* PLANT NAMED 'PKM02'**

(50) Latin Name: ***Campanula* hybrid**
Varietal Denomination: PKM02

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 59 days.

(21) Appl. No.: 13/694,585

(22) Filed: Dec. 14, 2012

(65) Prior Publication Data

US 2014/0173798 P1 Jun. 19, 2014

(51) Int. Cl.
*A01H 5/00* (2006.01)

(52) U.S. Cl.
USPC ..... Plt./414

(58) Field of Classification Search
USPC ..... Plt./414
See application file for complete search history.

(56) References Cited

PUBLICATIONS

Printout of application information from Community Plant Variety Office (CPVO) website for corresponding CPVO application No. 2012/2546 filed Nov. 15, 2012 (1 page) (http://www.cpvoextranet.cpvo.europa.eu).

Printout of application information from Japanese Plant Breeders' Rights application database for corresponding application No. 27644 filed Dec. 6, 2012 (1 page) (http://www.hinsyu.maff.go.jp/vips2/cmm/apCMM110.aspx?MOSS=1).

Printout of application information from Canadian Food Inspection Agency—Plant Varieties Journal No. 86 (Jan. 2013) for corresponding Canadian Plant Breeders' Rights application No. Dec. 7811 filed Dec. 14, 2012 (1 page) (http://www.inspection.gc.ca/english/plaveg/pbrpov/joubule.shtml).

*Primary Examiner* — Kent L Bell
(74) *Attorney, Agent, or Firm* — Foley & Lardner LLP

(57) ABSTRACT

A distinct cultivar of *Campanula* plant named 'PKM02' characterized by its broad campanulate flowers with a deeply lobed and reflexed corolla. The inflorescences are quite open with only a few small leaves.

5 Drawing Sheets

Figure 1:
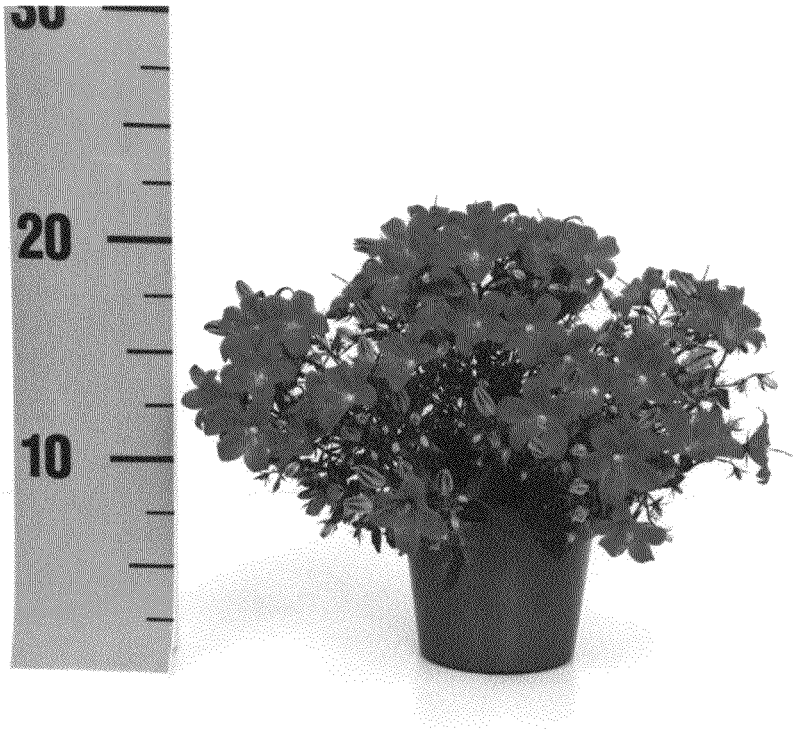

Latin name of genus and species of the plant claimed: *Campanula* hybrid.

Variety denomination: 'PKM02'.

BACKGROUND OF THE INVENTION

The present invention relates to a new and distinct cultivar of *Campanula* plant, botanically known as *Campanula* hybrid, common name Bellflower and hereinafter referred to by the name 'PKM02'.

The new *Campanula* originated from a planned cross between two different *Campanula* species; the female parent being an unnamed proprietary breeding line of *C. carpatica* (unpatented) and the male parent being an unnamed proprietary breeding line of *C. isophylla* (unpatented). Initial crossing was performed in 2009 by the Inventor followed by further testing and selection after vegetative propagation. Testing and selection started in 2009 and final selections were made October 2012.

Vegetative propagation occurred by terminal cuttings taken and propagated in Søhus, Denmark. Asexual reproduction of the new *Campanula* cultivar by terminal cuttings has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKM02'. These characteristics in combination distinguish 'PKM02' as a new and distinct cultivar:

1. Bushy elliptic plant form.
2. Broad campanulate violet (RHS between N88A and N88B) flowers with a deeply lobed and reflexed corolla.
3. Open inflorescence with only a few small leaves.

Plants of the cultivar 'PKM02' can be compared to plants of the *Campanula* cultivar 'PKM01' (U.S. patent application Ser. No. 13/507,741). However, in side-by-side comparisons conducted by the Inventor in Søhus, Denmark, 'PKM02' and 'PKM01' differ in the following characteristics:

1. 'PKM02' has darker violet flowers than 'PKM01'.
2. 'PKM02' has a more deeply lobed and reflexed corolla than 'PKM01'.
3. 'PKM02' has a less upright growth habit than 'PKM01'.

Compared with the parental breeding lines *C. carpatica* and *C. isophylla*, plants of the cultivar 'PKM02' differ in the following characteristics:

1. 'PKM02' has a less dense plant appearance than both parental lines.
2. 'PKM02' has flowers above the foliage whereas for *C. isophylla* new shoots partly grow above the flowers.
3. 'PKM02' has glabrous peduncles as compared to the pubescent peduncles of *C. carpatica*.
4. The sepals of 'PKM02' are in-between the parents with respect to length, width and reflexion, with *C. isophylla* having the longest, widest and least reflexed sepals.
5. 'PKM02' has darker violet flowers and a more deeply lobed corolla than the *C. carpatica* parental line.
6. 'PKM02' has a more reflexed corolla than the *C. isophylla* parental line.
7. 'PKM02' produce no or only small amounts of pollen whereas the parents produced large amounts of pollen.

8. 'PKM02' has a much smaller stigma than *C. carpatica* and a little smaller stigma than *C. isophylla*.

BRIEF DESCRIPTION OF THE PHOTOGRAPHS

The accompanying colored photographs illustrate the overall appearance of the new *Campanula* 'PKM02', showing the colors as true as it is reasonably possible to obtain in colored reproductions of this type. Colors in the photographs may differ slightly from the color values cited in the detailed botanical description, which more accurately describe the actual colors of 'PKM02'.

FIG. 1: The photograph comprises a side perspective view of a typical flowering plant of 'PKM02'.

Figure 2:
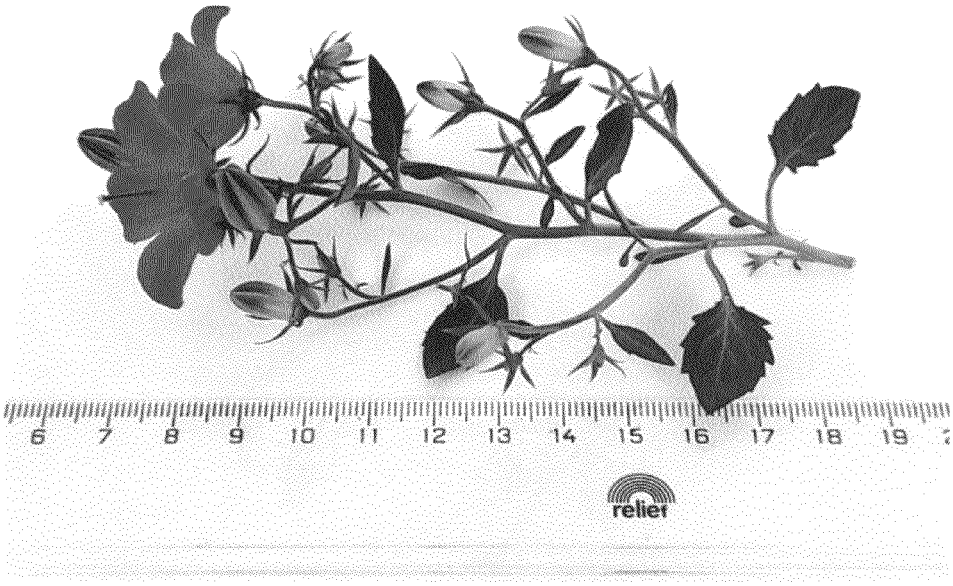

FIG. 2: The photograph comprises a close-up view of a typical inflorescence of 'PKM02'.

Figure 3:
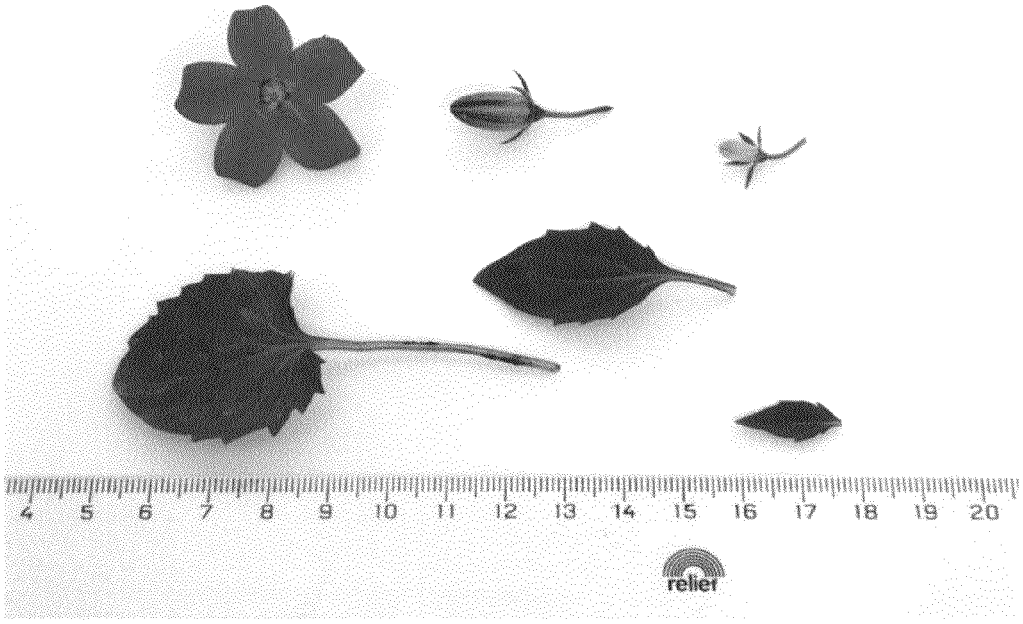

FIG. 3: The photograph comprises a close-up side view of a typical flower buds and leaves (from left: basal, middle and apical position) of 'PKM02'.

Figure 4:
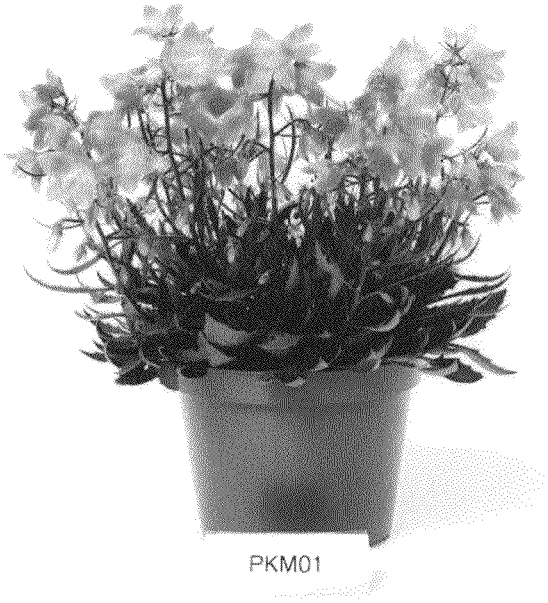

FIG. 4: The photograph comprises a side perspective view of a typical flowering plant of cultivar 'PKM01' (photo not taken at same time of year as FIG. 1; comparisons should consider this aspect).

Figure 5:
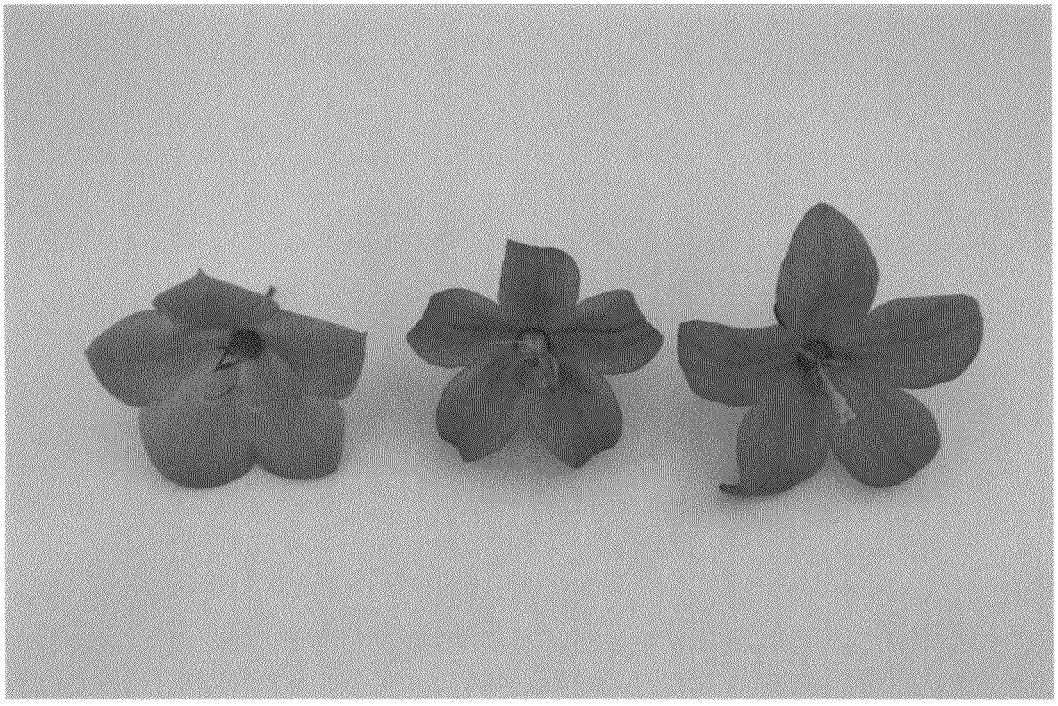

FIG. 5: The photograph comprises a close-up view of the flower of (as shown from left to right) the female parent (*C. carpatica*), 'PKM02' and the male parent (*C. isophylla*).

DETAILED BOTANICAL DESCRIPTION

The new *Campanula* 'PKM02' has not been observed under all possible environmental conditions. The phenotype of the new cultivar may vary with variations in environment such as temperature, light intensity, day length, and fertility level without any variance in genotype.

The aforementioned photographs, together with the following observations, measurements and values describe plants of the new *Campanula* 'PKM02' as grown under greenhouse conditions in an 11 cm pot.

The age of the 'PKM02' plants described is about 14 weeks after propagation. Color references are made to The Royal Horticultural Society Colour Chart (R.H.S.), 5$^{th}$ edition, except where general colors of ordinary significance are used.

Classification:

*Botanical*.—Campanula hybrid.

Parentage:

*Female or seed parent*.—Unnamed proprietary selection of *Campanula carpatica* (unpatented).

*Male or pollen parent*.—Unnamed proprietary selection of *Campanula isophylla* (unpatented).

Propagation:

*Type cutting*.—Terminal vegetative cuttings.

*Time to initiate roots*.—About 10 to 14 days at 18 to 21° C. in tunnels in a greenhouse.

*Root description*.—Fine, well branched.

Plant description:

*Form*.—Perennial, rosette plant with upright plant habit. Freely branching with basal shoots.

*Crop time*.—After rooting, about 14 weeks are required to produce finished flowering plants in 11 cm pots.

*Plant height* (*from soil level to top of plant plane*).—About 12-15 cm.

*Plant spread* (*width*).—About 16-19 cm.

*Vigor*.—Vigorous growth rate.

Foliage description:

*Leaf arrangement*.—Single.

*Leaf shape*.—Upper Leaves: Lanceolate. Lower Leaves: Ovate to Cordate.

*Leaf length*.—Basal: 25-35 mm. Apical: 10-25 mm.

*Leaf width*.—Basal: 20-40 mm. Apical: 10-25 mm.

*Margin*.—Dentate to Serrate, more prominent on basal than apical leaves.

*Color*.—Upper Surface, RHS N137B, Green. Lower Surface, RHS N137D, Green.

*Venation*.—Pattern: Pirmipalmate. Color: Upper Surface: A little paler than leaf blade ,between RHS 144B and 144C. Lower Surface: RHS 137D, Green.

*Petiole*.—Length: Basal: 40-60 mm. Apical: 10-20 mm. Color: A little paler than leaf blade, between RHS 144B and 144C.

Inflorescence description:

*Flower arrangement and shape*.—Broad campanulate flowers with deeply lobed and reflexed corolla. Upright to spreading arrangement. Inflorescences are panicles.

*Flower longevity*.—Longevity of individual flowers is highly dependent on temperature and light conditions. Flowers persistent.

*Inflorescence size*.—Length: 10-12 cm.

*Flowers*.—Quantity per inflorescence: 12-16. Length: 22-27 mm. Diameter: 30-40 mm. Arrangement and Shape: Single, sympetalous, campanulate, deeply lobed (½-⅔) and reflexed. Upright to outward aspect. Corolla Color, Upper and Lower Surfaces: Between RHS N88A and N88B, Violet.

*Sepals*.—Arrangement: Free. Appearance: Shiny and glabrous. Quantity per flower: 5. Length: 5-8 mm. Width: 0.5 mm. Overall shape: Deltoid. Apex: Acute. Margin: Entire. Color (mature and immature): Upper and lower surfaces: Green, RHS 137A. Pedicel: Length: 10-20 mm. Diameter: About 1 mm. Color: RHS 137B, Green.

*Buds*.—Length: Up to 18 mm. Diameter: Up to 7 mm. Shape: Elliptic, ridged. Color: Changes from yellow-green, between RHS 154B and 150C, to nearly the violet color of the flower (between RHS N88A and N88B). Coloration of buds starts at the tip.

Reproductive organs:

*Pistil*.—Quantity: 1. Length: 15-20 mm.

*Style*.—Length: 12-18 mm. Color: Light purple at base, dark purple in the middle and greyish purple (between RHS N92D and 90A) at the upper part.

*Stigma*.—Shape: Tripartite. Color: Greyish-Purple between RHS 91C, N92D and 90A. Anther: Shape: Fused; curling after shedding. Size: 1 mm. Color: RHS 158A. Pollen: Amount: None to very little.

High/low temperature tolerance: Not tested.

Disease resistance and/or susceptibility: Not tested.

I claim:

1. A new and distinct cultivar of *Campanula* hybrid plant named 'PKM02', as illustrated and described herein.

* * * * *